United States Patent
Kia et al.

(10) Patent No.: US 7,756,247 B2
(45) Date of Patent: Jul. 13, 2010

(54) METHOD AND APPARATUS FOR GENERATING A PANORAMIC IMAGE BY COMBINING IMAGE DATA GENERATED FROM MULTIPLE PERSPECTIVES

(75) Inventors: Omid Ebrahimi Kia, North Bethesda, MD (US); Krishnamoorthy Subramanyan, Palatine, IL (US); Paul Meredith Crawn, III, Richlandtown, PA (US)

(73) Assignee: Imaging Sciences International LLC, Hatfield, PA (US)

( * ) Notice: Subject to any disclaimer, the term of this patent is extended or adjusted under 35 U.S.C. 154(b) by 16 days.

(21) Appl. No.: 12/325,888

(22) Filed: Dec. 1, 2008

(65) Prior Publication Data

US 2009/0168954 A1 Jul. 2, 2009

Related U.S. Application Data

(63) Continuation of application No. 11/437,525, filed on May 20, 2006, now Pat. No. 7,460,638.

(60) Provisional application No. 60/682,971, filed on May 20, 2005.

(51) Int. Cl.
*A61B 6/14* (2006.01)
(52) U.S. Cl. .............................. 378/39; 378/38; 378/40
(58) Field of Classification Search .............. 378/38–40
See application file for complete search history.

(56) References Cited

U.S. PATENT DOCUMENTS 4,661,967 A 4/1987 Nishikawa (Continued)

FOREIGN PATENT DOCUMENTS

JP 4144548 A 5/1992

(Continued)

OTHER PUBLICATIONS

U.S. Appl. No. 11/437,525 non-final Office Action mailed Sep. 27, 2007, 9 pages.

(Continued)

*Primary Examiner*—Edward J Glick
*Assistant Examiner*—Thomas R Artman
(74) *Attorney, Agent, or Firm*—Michael Best & Friedrich LLP

(57) ABSTRACT

An apparatus for generating a panoramic image of part of a target, the apparatus including a source of penetrating radiation and a detector aligned with the source of penetrating radiation. The detector and source of penetrating radiation are rotate-able together with respect to the target. The detector has an array of radiation sensors arranged in rows and columns and is configured to output contents of each radiation sensor in the array of radiation sensors. The apparatus also includes a computer connected to the detector and configured to generate a panoramic image by combining data from sensors in the same row in different columns in different readout intervals, corresponding to different positions of the detector as it rotates with respect to the target. The combined outputs are selected to represent rays of radiation passing through a point on a defined curve. The computer is further configured to alter the defined curve and generate a second panoramic image using the altered curve and combing data from the sensor a second time.

10 Claims, 4 Drawing Sheets

U.S. PATENT DOCUMENTS

| | | |
|---|---|---|
| 4,856,038 A | 8/1989 | Guenther et al. |
| 5,195,114 A | 3/1993 | Sairenji et al. |
| 5,511,106 A | 4/1996 | Doebert et al. |
| 5,677,940 A | 10/1997 | Suzuki et al. |
| 5,784,429 A | 7/1998 | Arai |
| 6,049,584 A | 4/2000 | Pfeiffer |
| 6,289,074 B1 | 9/2001 | Arai et al. |
| 6,570,953 B1 | 5/2003 | Dobert et al. |
| 7,039,156 B2 | 5/2006 | Arai et al. |
| 7,460,638 B2 * | 12/2008 | Singh et al. .......... 378/39 |
| 7,545,909 B2 * | 6/2009 | Singh et al. .......... 378/39 |
| 2006/0274926 A1 * | 12/2006 | Singh et al. .......... 382/131 |
| 2007/0014461 A1 * | 1/2007 | Singh et al. .......... 382/128 |

FOREIGN PATENT DOCUMENTS

| | | |
|---|---|---|
| JP | 2001061834 A | 3/2001 |
| JP | 3621146 B2 | 2/2005 |

OTHER PUBLICATIONS

U.S. Appl. No. 11/437,525 Third-Party Submission of Prior Art in Published Application mailed Oct. 3, 2007, 38 pages.

PCT/US2006/019320 International Search Report and Written Opinion of the International Searching Authority mailed Feb. 11, 2008, 10 pages.

PCT/US2006/019320 International Preliminary Report On Patentability mailed Mar. 17, 2008, 6 pages.

* cited by examiner

METHOD AND APPARATUS FOR GENERATING A PANORAMIC IMAGE BY COMBINING IMAGE DATA GENERATED FROM MULTIPLE PERSPECTIVES

CROSS REFERENCE TO RELATED APPLICATIONS

This application is a continuation of prior-filed, co-pending U.S. patent application Ser. No. 11/437,525, filed on May 20, 2006, which issued as U.S. Pat. No. 7,460,638 on Dec. 2, 2008 and which claims the benefit of U.S. Provisional Patent Application No. 60/682,971, filed May 20, 2005.

This application incorporates by reference the following United States patent applications:

Ser. No. 11/437,523 entitled LOCATION OF ELONGATED OBJECT;

Ser. No. 11/437,524 entitled LOCATION OF CURVED STRUCTURE; and

Ser. No. 11/437,526 entitled PANORAMIC VIEW GENERATOR.

BACKGROUND

The invention relates to imaging a curved object in a panoramic array of data, and especially, but not exclusively, to panoramic imaging of the dental arch. The invention has particular application to imaging the maxilla, the mandible, or both in a dataset of part of the head of a human or other mammal.

In certain forms of dental medicine and surgery, a "panoramic" image of the jaw is used to examine the jaw, for example, for monitoring of dental health and condition, diagnosis, and planning of prosthetic and other surgical procedures. The panoramic image of the jaw, like a panoramic photograph, depicts the jaw as if it were imaged onto an imaginary approximately cylindrical sheet with the axis of the sheet upright, and the sheet were then unrolled into a flat form. However, the human jaw is not a perfect circular arc, so the "cylindrical" shape of the imaginary sheet is not exactly circular.

A panoramic x-ray image is conventionally made by placing the target between a source of x-rays and a detector of the x-rays and causing the source and the detector to rotate around the target. The source is collimated to produce a narrow fan of x-rays in a plane parallel to the axis of rotation, and the detector is arranged to expose a narrow strip of detecting surface aligned along the fan of x-rays. X-ray absorbing structures in the target cast an x-ray shadow on the detector strip. Any structure that is not exactly on the axis of rotation casts a shadow that moves across the strip as the source and detector rotate. In a conventional panoramic x-ray machine, the detector strip is part of an x-ray sensitive photographic film, exposed through a slit in a metal mask. By moving the film across the slit at a controlled speed, a part of the structure at a specific distance from the axis of rotation can be brought into sharp focus, because the shadow of the selected part of the structure follows the movement of the film exactly. More recent panoramic x-ray machines use a charge-coupled device (CCD) or a CMOS detector array, and a similar panoramic image can also be produced utilizing an Amorphous Silicon Flat Panel detector, which is also used in Cone Beam CT systems. By stepping the acquired charge across the detector array and integrating the image at a controlled speed, the focusing action of a moving film can be exactly imitated.

The human jaw is not an exact arc of a circle, so a simple circular motion of the source and detector, with the source, detector, and film transport or CCD stepping moving at a constant speed, does not provide a well-focused image of the whole jaw. Panoramic x-ray devices have been developed in which the focus position is adjusted so as to follow the actual curve of the jaw, either by a complicated movement of the x-ray source and/or detector, or by varying the rate of CCD readout, or both. However, such devices can adjust the focus position only at the time of x-ray exposure, and only to a pre-programmed jaw contour. If the actual jaw does not match the pre-programmed contour, or if the jaw is not in exactly the expected position relative to the scanner, an incorrectly focused image may result, in which the plane of sharp focus diverges from the jaw for all or part of the dental arch.

The depth of focus can be adjusted by adjusting the width of the detecting strip. A narrower detector strip gives a deeper area of sharp focus, at the expense of requiring either a more intense or a slower exposure to achieve the same level of saturation of the x-ray film or CCD pixels.

SUMMARY

With pre-existing panoramic x-ray devices, the strip width can be adjusted only at the time of exposure. There is therefore a hitherto unfulfilled need for a system by which the line of sharp focus and/or the depth of focus in a panoramic x-ray can be adjusted after the x-ray exposure.

According to one embodiment, the invention provides a method and apparatus for generating a panoramic image of part of a target, the device comprising: a source of penetrating radiation; a detector aligned with the source of penetrating radiation, the detector and source of penetrating radiation rotate-able together with respect to the target, the detector having an array of radiation sensors arranged in rows and columns, the detector configured to output contents of each radiation sensor in the array of radiation sensors; and a computer connected to the detector and configured to generate a panoramic image by combining data from sensors in the same row in different columns in different readout intervals, corresponding to different positions of the detector as it rotates with respect to the target, the combined outputs being selected to represent rays of radiation passing through a point on a defined curve, the computer further configured to alter the defined curve and generate a second panoramic image using the altered curve and combing data from the sensor a second time.

In one embodiment, the computer is configured to select staggered sets of readout intervals to focus on different points of the target. In another embodiment, the computer is configured to change a focus on a point within the target. In yet another embodiment, the computer is configured to modify specific readout intervals or sensor positions for specific columns of sensors in the array of radiation sensors. In still another embodiment, the computer is configured to increase a depth of a focal trough. In still another embodiment, the computer is configured to increase the depth of a focal trough by reducing the number of sensor outputs combined.

The invention also provides a device for generating a panoramic image of part of a target, the device comprising: a source of penetrating radiation; a detector aligned with the source of penetrating radiation, the detector and source of penetrating radiation rotate-able together with respect to the target, the detector having an array of radiation sensors arranged in rows and columns, the detector configured to output contents of each radiation sensor in the array of radiation sensors; and a computer connected to the detector and configured to generate a panoramic image by combining data from sensors in the same row in different columns in different readout intervals, corresponding to different positions of the detector as it rotates with respect to the target, the combined outputs being selected to represent rays of radiation passing through a point on a defined curve, the computer further configured to generate a second panoramic image by combining data from the sensors a second time.

In one embodiment, the computer is configured to select staggered sets of readout intervals to focus on different points of the target. In another embodiment, the computer is configured to change a focus on a point within the target. In yet another embodiment, the computer is configured to modify specific readout intervals or sensor positions for specific columns of sensors in the array of radiation sensors.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Figure 1:
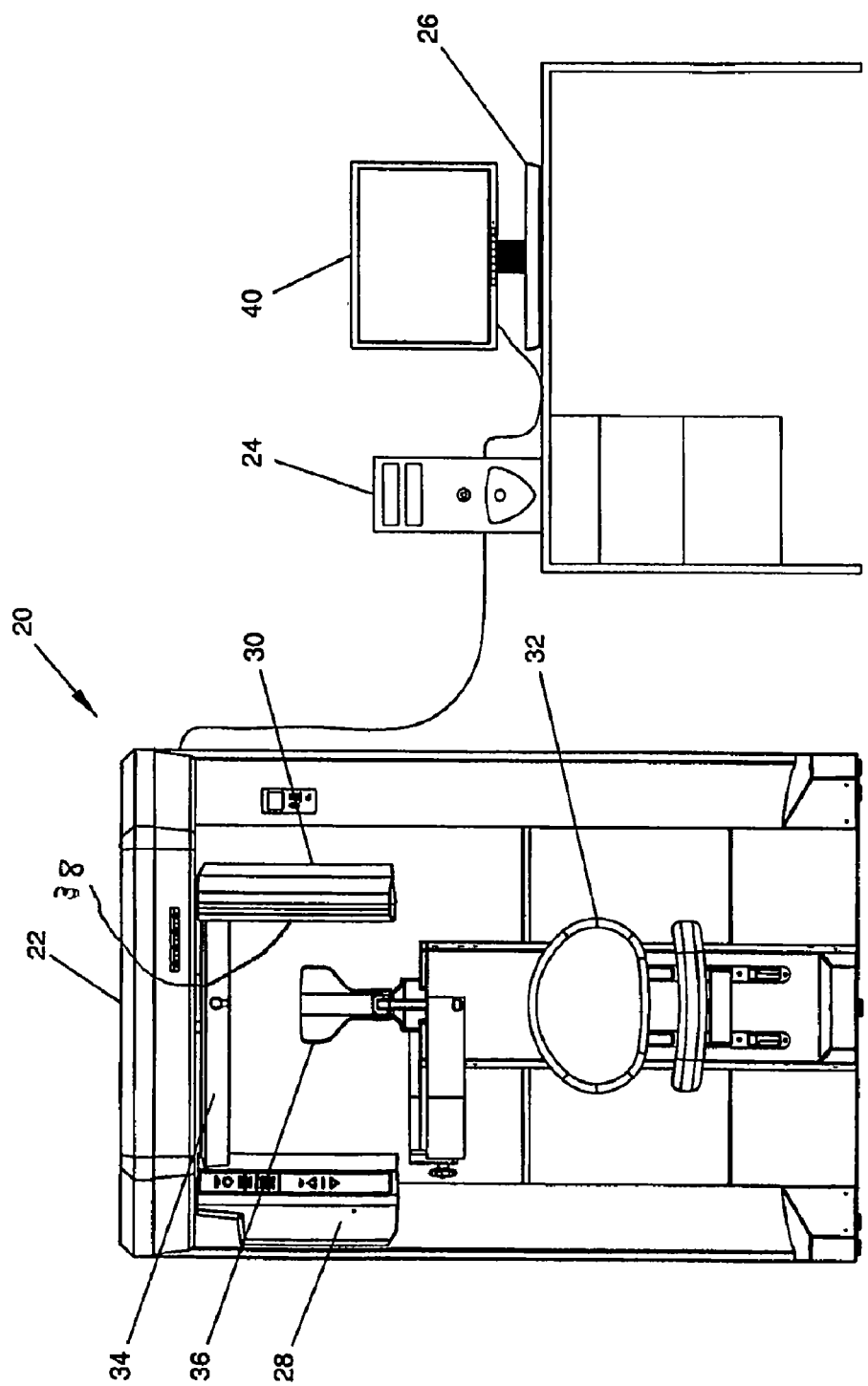
FIG. 1 is a schematic view of apparatus for generating a tomographic image.

It is to be understood that both the foregoing general description and the following detailed description are exemplary and explanatory and are intended to provide further explanation of the invention as claimed. Before any embodiments of the invention are explained in detail, it is to be understood that the invention is not limited in its application to the details of construction and the arrangement of components set forth in the following description or illustrated in the drawings. The invention is capable of other embodiments and of being practiced or of being carried out in various ways.

Figure 2:
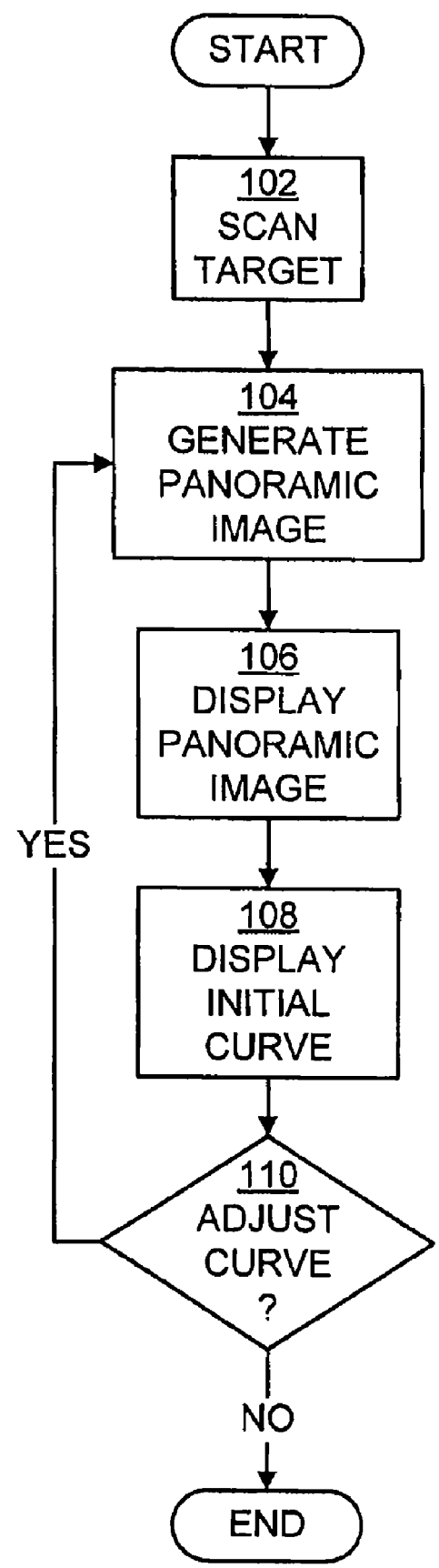
FIG. 2 is a flow chart of one embodiment of a method according to the invention.
Figure 6:
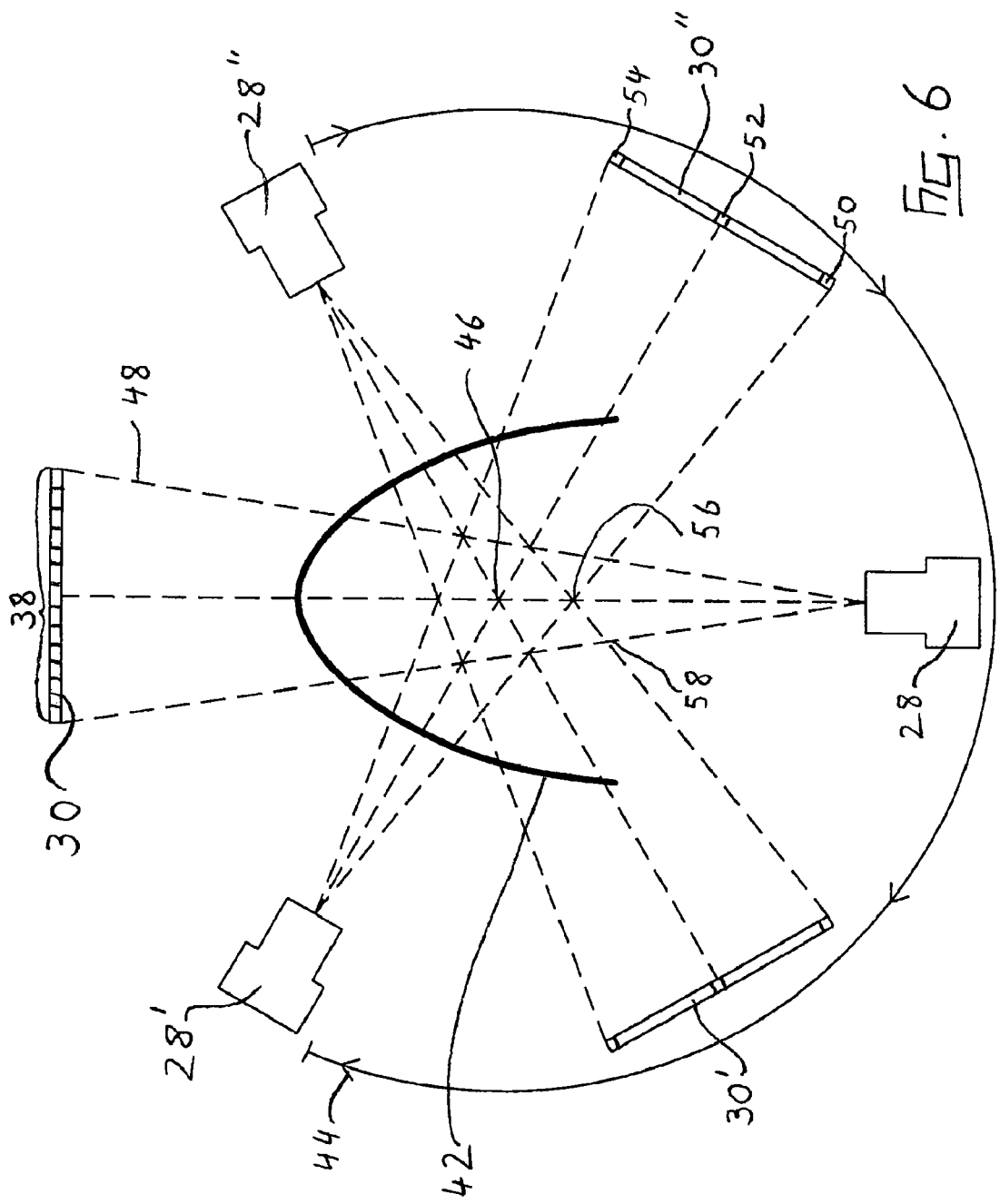
FIG. 6 is a schematic plan view of part of the apparatus of FIG. 1 in operation.

Referring to the drawings, and initially to FIGS. 1, 2, and 6, one form of tomographic apparatus according to an embodiment of the invention, indicated generally by the reference numeral 20, comprises a scanner 22 and a computer 24 controlled by a console 26 with a display 40. The scanner 22 comprises a source of x-rays 28, an x-ray detector 30, and a support 32 for an object to be imaged. In an embodiment, the scanner 22 is arranged to image the head, or part of the head, of a human patient (not shown), especially the jaws and teeth, shown symbolically by the contour line 42 in FIG. 6. The support 32 may then be a seat with a rest or restrainer 36 for the head or face (not shown) of the patient. The x-ray source 28 and detector 30 are then mounted on a rotating carrier 34 so as to circle round the position of the patient's head, while remaining aligned with one another, as shown by the arrow 44 in FIG. 6.

The x-ray source 28 is arranged to emit a fan-shaped beam of x-rays 48, with the plane of the fan parallel to the axis of rotation 46 of the scanner 22, vertical as seen in FIG. 1 and perpendicular to the plane of FIG. 6. The x-ray detector 30 has an array of sensors in the form of pixels 38 aligned with the fan-shaped beam of x-rays. The array of sensors is long enough to receive the whole imaging part of the fan, and is several pixels wide. The scanner 22 may be a cone-beam computed tomographic scanner, with the x-ray beam collimated down to a narrow fan. Suitable apparatus is available commercially, for example, the i-CAT Cone Beam 3-D Dental Imaging System from Imaging Sciences International of Hatfield, Pa. The part of the x-ray detector 30 not within the fan may then be masked off, or may simply be inactive, so that any data received by sensors 38 outside the fan is discarded. Alternatively, the scanner 22 may be a dedicated panoramic scanner, in which the x-ray source 28 produces only a fan-shaped beam and the array of sensors 38 consists only of the strip facing the fan-shaped beam.

The detector 30 is arranged to read out the contents of every sensor 38 separately, without integrating across rows. Non-integrated readout may be achieved by the design of the detector 30, or may be achieved by operating the x-ray source 28 in pulses, and/or by reading out the detector between pulses. The scanner 22 may then be rotated by, for example, one or more pixel widths of the detector 30 between pulses.

Referring now to FIG. 2, in step 102, the x-ray detector 30 produces a stream of x-ray data from the sensors 38. Each sensor output represents the total density of a line 48 through the patient's head at a known alignment. At each readout interval, each column of sensors 38 represents lines forming a vertical fan. The different columns of sensors represent lines forming different fans spread apart sideways. If the scanner follows a simple circular motion, the middle of the fan is typically on the axis 46.

The computer 24 receives the x-ray image data from the scanner 22, and in step 104 calculates a panoramic image by summing data from sensors in the same row in different columns in different readout intervals, corresponding to different positions of the detector 30. The summed data then represent intersecting lines 48 through the patient's head. By selecting specific readout intervals or sensor positions for specific columns, lines can be chosen that intersect at a specific point within the patient's head. Then, the density information for the specific point in all the lines sum additively, whereas the density data for other points in the lines, which are to a greater or lesser extent independent, tend to sum randomly, and partly cancel out. The specific point is thus brought into focus. Typically, the selected readout intervals will be in order, but not necessarily evenly spaced, from one side of the detector strip to the other.

For example, in FIG. 6, the x-ray source 28 and the detector 30 are shown in three exemplary positions as 28, 28', 28" and 30, 30', 30", and three exemplary x-ray lines 48 are shown at each position from the x-ray source 28 to a leading sensor position 50, a middle sensor position 52, and a trailing sensor position 54 of the array of sensors 38. FIG. 6 shows seven points 46, 56 where three exemplary rays 48 meet, and a further six points 58 where two exemplary rays 48 meet. It may be seen how each of those points may be selected by a suitable choice of sensor 50, 52, 54 or none of those sensors at each of the positions 28, 28', 28". By using a larger number of positions 28, 28', 28", etc. of the x-ray source and positions 30, 30', 30", etc. of the detector, and by making suitable selections from among the sensors 38 at each position, any point within the region of the jaw 42 or other target can be selected to an accuracy comparable to the size of the detector sensors 38.

In a practical embodiment, fewer than all of the rays 48 suggested by FIG. 6 may be used for a specific point 46, 56, 58. In particular, some of the points 56, 58 are at the intersections of some rays between the source 28 and the axis 46, and are at the intersections of other rays between the axis 46 and the detector 30. Because the x-rays 48 are fanning out vertically more than they are fanning out circumferentially, gathering every possible ray 48 through a point 56, 58 above or below the center of the source 28 requires selecting sensors 38 in different rows of the detector 30, as well as in different columns. Where the target is a contour 42 at approximately a constant distance from the axis 46, and only the rays 48 passing through a chosen point on the contour 42 between the axis 46 and the detector 30 are selected, then a summation of detector outputs from a single horizontal row of detector sensors can be used with only slight vertical blurring.

However, as may be seen from the example of the points 58 in FIG. 6, for a point further away from the center axis 46 than the width of the x-ray fan at the axis, not all positions of the detector 30 will produce a sensor position representing an x-ray line 48 through that point. In particular, the outer points 58 are typically seen only on x-ray lines close to a radial direction from the center axis 46 to the point in question, and not on x-ray lines at a high angle to that radial direction. Consequently, the voxel represented by an image pixel is typically not approximately cubic, but is elongated in the radial direction. As the scanner 22 rotates, an object feature that is radially inside or outside the selected point 58 advances across the sensors 38 at a different speed from the selected point 58, and is summed into different image pixels at successive readout intervals. As a result, the object feature becomes in effect smeared out across different image pixels, rather than being focused in a single image pixel. The wider the fan, or the greater the distance between the first and last active detector sensor positions 50, 54, the greater the number of image pixels over which any given object feature is smeared out, and the more pronounced the defocusing becomes. As a result, a narrow fan leads to a greater radial depth of focus. As will be explained below, this phenomenon can be used to advantage.

In accordance with the present embodiment of the invention, the output from each detector sensor 38 at each readout interval, corresponding to successive positions of the detector 30, 30', 30", etc., is recorded separately. The sensors are not integrated across the detector array by indexing the CCD cell contents backward one sensor at a time as the detector 30 is moved forward. The summing of selected sensors from selected readout intervals is done in software after the scanning is completed. It is therefore possible to repeat the summing process as often as desired.

By repeating the summing process selecting a different set of readout intervals, a different point in the patient's head is brought into focus. By selecting systematically staggered sets of readout intervals, a series of points forming a curve within the patient's head, for example, a series of points lying on an estimate of the contour 42 of the patient's dental arch, can be brought into focus. By repeating the same set of sums for each horizontal row of detector sensors, a vertical surface following the curve can be brought into focus, creating a panoramic image of the patient's dental arch.

The depth of the region around the selected curve that is in effectively sharp focus is known as the "focal layer thickness" or "focal trough." For dental work, where the panoramic view is essentially an elevation view of the dental arch, or a large part thereof, as seen from the inside or the outside, a view with fine detail in the vertical and circumferential directions, but considerable focal trough depth in the radial direction, perpendicular to the plane of the image, is frequently desirable. Data from object features outside the effective focal trough are "smeared" out over different image pixels to such an extent that they contribute little to the final image. The wider the strip of sensors 38 used to sum the image points is, the more rapidly the data will cease to be related and become smeared as the distance from the selected image point at the center of the focal trough increases, and thus the smaller is the depth of focus of the final image.

In step 106, the resulting panoramic image is displayed to a user on the monitor 40.

In describing step 104, the system for choosing the curve 42 on which the selected points of focus lie was not explained. The initial curve 42 may be arbitrary. Typically, the initial curve is a conventional estimate of the contour of a patient's dental arch. However, different patients have dental arches of different shapes and sizes and, even using the headrest 36, different patients may not be positioned in exactly the same position in the scanner 22. When the panoramic image is inspected in step 106, it may become apparent to the user that the curve 42 on which the panoramic image is based does not entirely agree with the actual contour of the patient's dental arch. If the disagreement is greater than half the thickness of the focal trough, the image does not bring the whole jaw into sharp focus.

Figure 5:
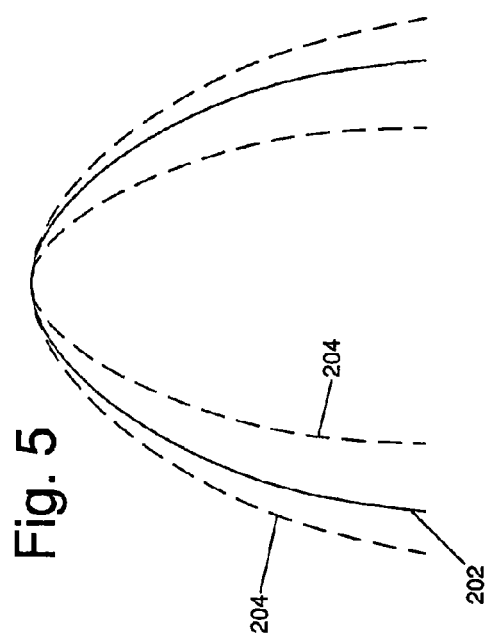
FIG. 5 is a schematic view similar to FIG. 3.
Figure 4:
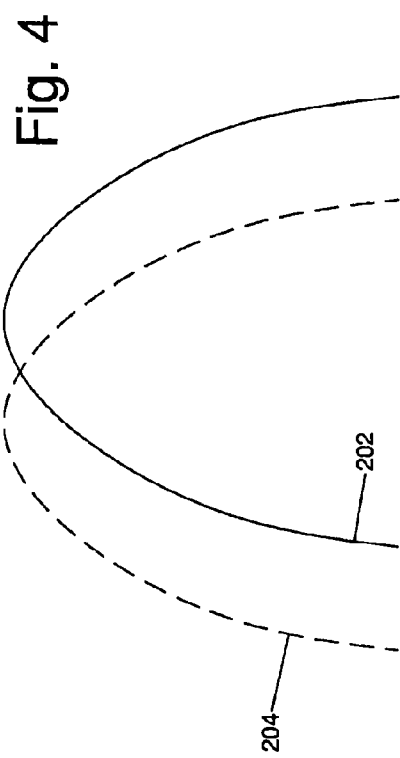
FIG. 4 is a schematic view similar to FIG. 3.
Figure 3:
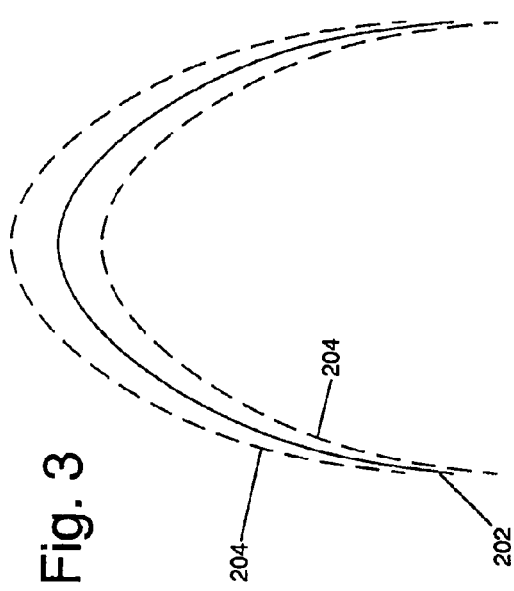
FIG. 3 is a schematic view of a display of curves representing a contour of a jaw.

Referring now also to FIGS. 3 to 5, in step 108 an image 202 of the shape of the initially selected curve 42 in plan view is displayed on the monitor 40. The monitor 40 also displays a control curve 204 that can be moved by the user. In FIGS. 3 to 5, the initial curve 202 is shown in a continuous line, and the control curve 204 is shown in a broken line. In a practical embodiment, the curves 202, 204 may be shown on the monitor 40 as, for example, lines of different colors or different weights.

In step 110, the user may be allowed to move the control curve 204 backwards and forwards relative to the general orientation of the jaw, as shown in FIG. 3, or sideways, as shown in FIG. 4. The user may be allowed to make the control curve 204 wider or narrower, as shown in FIG. 5. The user may be allowed to rotate the control curve 204. The adjustments may be made by using cursor or other keys on a keyboard, or by dragging the control curve 204 on screen, or by dragging handles attached to the control curve on screen.

Especially when dragging the control curve 204 on screen, more elaborate changes of position are possible. For example, the user may be permitted to lock down parts of the control curve 204 that are correctly focused, while moving parts of the control curve that are not yet correctly focused, or may be able to drag the curve into a different shape.

The process then returns to step 104, and computes a new panoramic image from the original recorded data from the detector 30, using the control curve 204, instead of the original curve 42, 202, to select the focus points. Steps 104 through 110 may be repeated as often as necessary or desirable. For example, the user may continue to adjust the control curve 204 until the user decides that he or she has achieved an adequately sharp image, or the sharpest practical image, of the dental arch in the panoramic display in step 106.

Where the computer 24 has sufficient processing power, the panoramic image may be updated in real time, or substantially in real time, as the user adjusts the control curve 204. The panoramic image and the control curve 204 may then be displayed side by side on the monitor 40, allowing the user to see the effect of adjustments to the control curve as the user adjusts the control curve.

The focal trough depth can be increased by shortening the row of sensors 38 from which the outputs are summed in step 104. However, reducing the number of sensors summed typically reduces the overall quality of the image, and is usually advantageous only when a deep focal trough is desired in a special case to supplement and/or augment the diagnostic information.

Various modifications and variations can be made in the present invention without departing from the spirit or scope of the invention. Thus, it is intended that the present invention cover modifications and variations of this invention provided they come within the scope of the appended claims and their equivalents.

What is claimed is:

1. A device for generating a panoramic image of part of a target, the device comprising:
    a source of penetrating radiation;
    a detector aligned with the source of penetrating radiation, the detector and source of penetrating radiation rotateable together with respect to the target, the detector having an array of radiation sensors arranged in rows and columns, the detector configured to output contents of each radiation sensor in the array of radiation sensors; and
    a computer connected to the detector and configured to generate a panoramic image by combining data from sensors in the same row in different columns in different readout intervals, corresponding to different positions of the detector as it rotates with respect to the target, the combined outputs being selected to represent rays of radiation passing through a point on a defined curve, the computer further configured to alter the defined curve and generate a second panoramic image using the altered curve and combing data from the sensor a second time.

2. A device as claimed in claim 1, wherein the computer is configured to select staggered sets of readout intervals to focus on different points of the target.

3. A device as claimed in claim 1, wherein the computer is configured to change a focus on a point within the target.

4. A device as claimed in claim 3, wherein the computer is configured to modify specific readout intervals or sensor positions for specific columns of sensors in the array of radiation sensors.

5. A device as claimed in claim 1, wherein the computer is configured to increase a depth of a focal trough.

6. A device as claimed in claim 5, wherein the computer is configured to increase the depth of a focal trough by reducing the number of sensor outputs combined.

7. A device for generating a panoramic image of part of a target, the device comprising:
    a source of penetrating radiation;
    a detector aligned with the source of penetrating radiation, the detector and source of penetrating radiation rotateable together with respect to the target, the detector having an array of radiation sensors arranged in rows and columns, the detector configured to output contents of each radiation sensor in the array of radiation sensors; and
    a computer connected to the detector and configured to generate a panoramic image by combining data from sensors in the same row in different columns in different readout intervals, corresponding to different positions of the detector as it rotates with respect to the target, the combined outputs being selected to represent rays of radiation passing through a point on a defined curve, the computer further configured to generate a second panoramic image by combing data from the sensors a second time.

8. A device as claimed in claim 7, wherein the computer is configured to select staggered sets of readout intervals to focus on different points of the target.

9. A device as claimed in claim 7, wherein the computer is configured to change a focus on a point within the target.

10. A device as claimed in claim 9, wherein the computer is configured to modify specific readout intervals or sensor positions for specific columns of sensors in the array of radiation sensors.

* * * * *